United States Patent [19]

Nohara et al.

[11] Patent Number: 4,769,456

[45] Date of Patent: Sep. 6, 1988

[54] SULFENAMIDE DERIVATIVES AND THEIR PRODUCTION

[75] Inventors: Akira Nohara; Yoshitaka Maki, both of Kyoto, Japan

[73] Assignee: Takeda Chemical Industries, Ltd., Osaka, Japan

[21] Appl. No.: 14,352

[22] Filed: Feb. 13, 1987

[30] Foreign Application Priority Data

Feb. 13, 1986 [JP] Japan ................................ 61-29569

[51] Int. Cl.$^4$ .......................................... C07D 513/22
[52] U.S. Cl. ...................................................... 544/9
[58] Field of Search ........................................... 544/9

[56] References Cited

U.S. PATENT DOCUMENTS 4,636,499  1/1987  Brandstrom et al. .................... 544/9

FOREIGN PATENT DOCUMENTS 0171372  2/1986  European Pat. Off. .

Primary Examiner—John M. Ford
Attorney, Agent, or Firm—Wegner & Bretschneider

[57] ABSTRACT

The compound of the formula

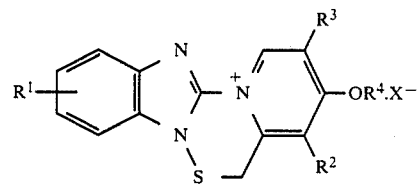

wherein $R^1$ is hydrogen, methoxy or trifluormethyl, $R^2$ and $R^3$ are the same or different and are each hydrogen or methyl, $R^4$ is a fluorinated lower alkyl having 2 to 5 carbon atoms and 1 to 11 fluorine atoms and $X^-$ is a pharmaceutically acceptable anion, respectively, possesses both strong antisecretory activity and gastric mucosal protective activity, which is produced by reacting a pyridine derivative of the formula

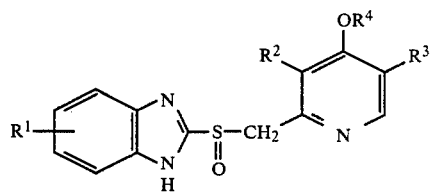

wherein $R^1$, $R^2$, $R^3$ and $R^4$ have the same meaning as defined above, with an acid.

15 Claims, No Drawings

SULFENAMIDE DERIVATIVES AND THEIR PRODUCTION

The present invention relates to sulfenamide derivatives, which work well as antiulcer drugs etc., and the method of their production.

Pyridine derivatives possessing antiulcer activity include the compound described in U.S. Pat. No. 4,255,431 (corresponding to Japanese Unexamined Patent Laid-open No. 141783/1979), which is known to suppress the secretion of gastric acid by inhibiting $H^+$, $K^+$-ATPase in the stomach. It has been pointed out that the inhibition of $H^+$, $K^+$ATPase by such pyridine derivatives are not due to the compounds themselves, but due to the products of their conversion in European Patent Publication No. 171,372A (Japanese Unexamined Patent Laid-open No. 7281/1986).

The compounds described in the European Patent Publication No. 171,372A require improvements in relation to stability, absorbability, antiulcer effect, antisecretory activity, etc.

The present inventors made further studies, focusing on their attention on the problems mentioned above, and completed the present invention.

The present invention relates to:
(1) Sulfenamide derivatives expressed by the formula

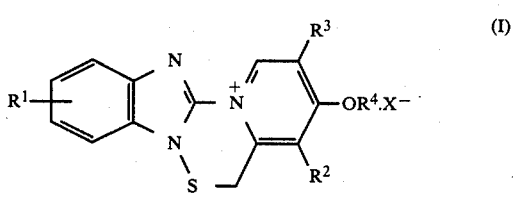

wherein $R_1$ is hydrogen, methoxy or trifluoromethyl $R^2$, and $R^3$ are the same or different and are each hydrogen or methyl, $R^4$ is a fluorinated lower alkyl group having 2 to 5 carbon atoms and 1 to 11 fluorine atoms and $X^-$ is an anion, respectively, and (2) A method for producing, sulfenamide derivatives of the formula (I), which comprises reacting pyridine derivatives of the formula

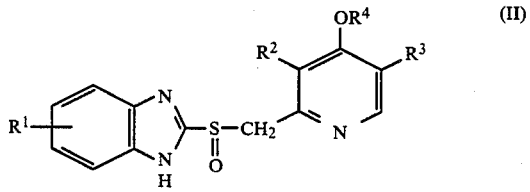

wherein $R^i$ is hydrogen, methoxy or trifluoromethyl, $R^2$ and $R^3$ are the same or different and are each hydrogen or methyl, and $R^4$ is a fluorinated lower alkyl group having 2 to 5 carbon atoms with an acid.

Fluorinated lower alkyls having 2 to 5 carbon atoms and 1 to 11 fluorine atoms, preferably 3 to 8 fluorine atoms, which are represented by $R^4$ in the formulas shown above, include 2,2,2-trifluoroethyl 2,2,3,3,3-pentafluoropropyl, 2,2,3,3-tetrafluoropropyl, 1-trifluoromethyl-2,2,2-trifluoroethyl, 2,2,3,3,4,4,4-heptafluorobutyl and 2,2,3,3,4,4,5,5-octafluoropentyl etc.

Anions represented by $X^-$ include $Cl^-$, $Br^-$, $I^-$, $SO_4^{2-}$, $CH_3SO_3^-$,

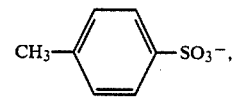

$PO_4^{3-}$, $ClO_4^-$, $BF_4^-$, $PF_6^-$ and $AuCl_4^-$ etc., which are derived from a pharmaceutically acceptable acid.

Sulfenamide derivative (I), the desired compound of the present invention, can be produced by heating (from about 40° to 100° C.) pyridine derivative (II), which can be obtained by the method described later; however, it is preferable that the desired compound be produced by reacting the pyridine derivative with an acid. Acids which can be used include hydrochloric acid, hydrobromic acid, hydriodic acid, phosphoric acid, sulfuric acid, perchloric acid, methanesulfonic acid, p-toluenesulfonic acid, fluoboric acid, hexafluorophosphoric acid and hydrogen tetrachloroaurate; they are used usually in an equivalent of 1 to 2~5. Solvents to be used include alcohols such as methanol, ethanol and propanol; water, acetone, acetonitrile, chloroform and dichloromethane etc. Reaction temperature should be chosen in the range of ice-cooling temperature to 60° C.; reaction time should be between several minutes and 24 hours.

The desired compound (I), produced via the reaction described above, can be separated and purified using a conventional method such as recrystallization or chromatography etc.

The production method for the starting material (II) is hereinafter explained.

The compound (II) can be produced by subjecting the compound of the formula

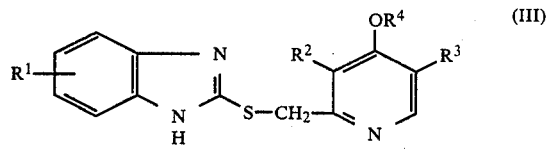

wherein $R^l$, $R^2$, $R^3$ and $R^4$ have the same meaning as defined above, to oxidation.

Oxdizing agents to be used for this purpose include peracids such as m-chloroperbenzoic acid, peracetic acid, trifluoroperacetic acid and permaleic acid; sodium bromite; and sodium hypochlorite etc. Solvents to be used for the reaction include halogenated hydrocarbons such as chloroform and dichloromethane; ethers such as tetrahydrofuran and dioxane; amides such as dimethylformamide; and water etc. These solvents can be used either singly or in combination. It is recommended that said oxidizing agents are used in an amount of about 1 equivalent to slightly excess relative to the compound (III), i.e., about 1 to 3 equivalent, preferably about 1 to 1.5 equivalent. Reaction temperature can be chosen in a range of ice-cooling temperature to the boiling point of the used solvent, generally ice-cooling temperature to room temperature, preferably about 0° C. to 10° C. Reaction time should be about 0.1 to 24 hours, preferably about 0.1 to 4 hours.

The compound (III) can be produced by reacting the compound of the formula

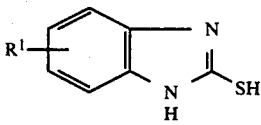

wherein R¹ has the same meaning as defined above with the compound of the formula

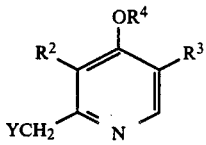

wherein R², R³ and R⁴ have the same meaning as defined above, and Y is a halogen atom.

Halogen atoms represented by Y include, for example, chlorine, bromine and iodine.

It is preferable that the reaction is carried out in the presence of a base. Bases to be used include alkali metal hydrides such as sodium hydride and potassium hydride etc., alkali metal such as metallic sodium etc., sodium alcoholates such as sodium methoxide and sodium ethoxide etc., alkali metal carbonates such as potassium carbonate and sodium carbonate etc., and organic amines such as triethylamine and so on. Solvents to be used for the reaction include alcohols such as methanol and ethanol, and dimethylformamide and so on. Said bases are usually used in an amount of 1 equivalent to slightly excess, but can be used in an equivalent of much more than 1. It is recommended that they are used in an equivalent of about 2 to 10, preferably about 2 to 4. Reaction temperature should be between about 0° C. and around the boiling point of the used solvent, preferably betweem about 20° C. and 80° C. Reaction time should be 0.2 to 24 hours, preferably about 0.5 to 2 hours.

The compound (V) can be produced as follows:

Method (1)

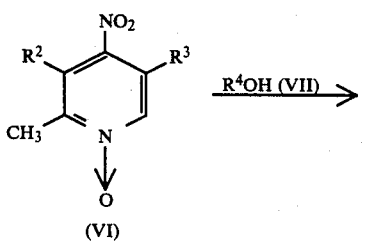

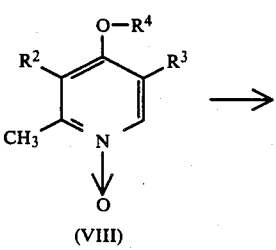

-continued
Method (1)

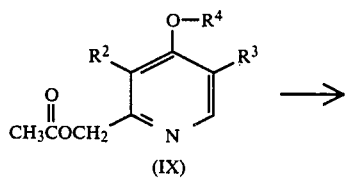

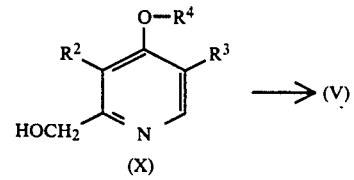

The alkoxy derivative of the formula (VIII) wherein R², R³ and R⁴ have the same meaning as defined above can be produced by reacting the nitro compound of the formula (VI) wherein R² and R³ have the same meaning as defined above with the alcohol derivative R⁴OH (VII) wherein R⁴ has the same meaning as defined above in the presence of a base. Bases to be used for this reaction include alkali metals such as lithium, sodium and potassium, alkali metal hydrides such as sodium hyride and potassium hydride, alcohlates such as potassium t-butoxide and sodium propoxide, alkali metal carbonates or hydrogen carbonates such as potassium carbonate, lithium carbonate, potassium hydrogen carbonate and sodium hydrogen carbonate, and alkali hydroxides such as sodium hydroxide and potassium hydroxide and so on. Solvents to be used for the reaction include R⁴OH itself, ethers such as tetrahydrofuran and dioxane etc., ketones such as acetone and methyl ethyl ketone etc., acetonitrile, dimethylformamide, and hexamethylphosphoric triamide and so on. Reaction temperature can be chosen in a range of ice-cooling temperature to around the boiling point of the solvent. Reaction time should be about 1 to 120 hours.

The compound (VIII), obtained as described above, is then heated (from about 80° to 120° C.) in the presence of either acetic anhydride alone or both acetic anhydride and a mineral acid such as sulfuric acid and perchloric acid to yield the 2-acetoxymethylpyridine derivative of the general formula (IX) wherein R², R³ and R⁴ have the same meaning as defined above. Reaction time should be generally about 0.1 to 10 hours.

The compound (IX) is then subjected to alkali hydrolysis to produce the 2-hydroxymethylpyridine derivative of the formula (X) wherein R², R³ and R⁴ have the same meaning as defined above. The alkalis to be used for the hydrolysis include, for example, sodium hydroxide, potassium hydroxide, potassium carbonate and sodium carbonate etc. Solvents to be used include, for example, methanol, ethanol and water etc. The reaction should be generally carried out at about 20° to 60° C. for about 0.1 to 2 hours.

The compound (X) is then halogenated with a halogenating agent such as thionyl chloride to produce the 2-halogeno-methylpyridine derivative of the formula (V) wherein R², R³ and R⁴ have the same meaning as defined above; and γ is chlorine, bromine, or iodine. Solvents to be used for this reaction include chloroform, dichloromethane and tetrachloroethane etc. The reaction should be generally carried out at about 20° to 80° C. for about 0.1 to 2 hours.

The compound (V), produced as described above, is a salt of hydrohalogenic acid corresponding to the used halogenating agent; it is preferable that it is used immediately for the reaction with the compound (IV).

Method (2)

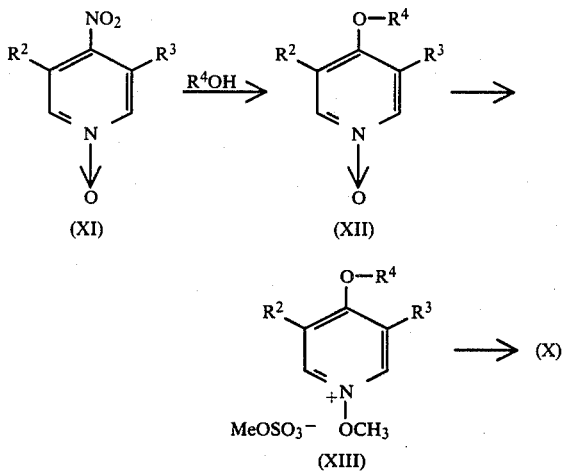

Using the same reaction as that in Method (1), the compound of the formula (XI) wherein $R^2$ and $R^3$ have the same meaning as defined above is derivatized to the compound of the formula (XII) wherein $R^2$, $R^3$ and $R^4$ have the same meaning as defined above.

The compound (XII) is then methylated with dimethyl sulfate to the compound of the formula (XIII) wherein $R^2$, $R^3$ and $R^4$ have the same meaning as defined above. This reaction usually requires no solvent, reaction temperature should be about 100° to 120° C. and reaction time should be about 0.1 to 4 hours.

The compound (X) can be produced by reacting the compound (XIII) with a radical source such as ammonium persulfate or another persulfate in methanol. Reaction temperature should be about 20° to 80° C. and reaction time should be between about 0.5 and 4 hours.

The compound (I), the desired compound produced by the method described above, possessing antiulcer activity, antisecretory activity, mucosal protective activity, etc., can be used as a therapeutic drug for digestive ulcers.

When the compound (I) of the present invention is used to treat a mammal for peptic ulcers, it can be orally administered in the dose form of a capsule, tablet, granule, or others, in combination with a pharmacologically acceptable carrier, excipient, diluent, etc. Its dose should be about 0.01 ~ 30 mg/kg/day, preferably about 0.1 ~ 3 mg/kg/day The production methods for the starting compounds used for the present invention and those for the compound (I) of the present invention, are each hereinafter described concretely with some reference and working examples.

REFERENCE EXAMPLE 1

2,3-Dimethyl-4-nitropyridine-1-oxide (2 g) was dissolved in 2,2,3,3-tetrafluoropropanol (10 ml). To the resultant solution potassium t-butoxide (1.6 g) was added gradually at room temperature, after which the solution was heated at 80° ~ 90° C. for 22 hours. The resulting reaction mixture was diluted with water, extracted with chloroform, dried over magnesium sulfate, concentrated, applied on silica gel (70 g) column, eluted with methanol-chloroform (1:10) and then recrystallized from ethyl acetate-hexane to give 2.6 g of 2,3-dimethyl-4-(2,2,3,3-tetrafluoropropoxy)pyridine-1-oxide as color less needles (melting point: 138° ~ 139° C.).

Using the same procedure as described above, the compounds (VIII) were produced using the compounds (VI) as the starting materials.

| Compound (VIII) | | | |
|---|---|---|---|
| $R^2$ | $R^3$ | $R^4$ | Melting point (°C.) |
| H | H | $CH_2CF_3$ | 148 ~ 150 |
| $CH_3$ | $CH_3$ | $CH_2CF_3$ | 138 ~ 139 |

REFERENCE EXAMPLE 2

A mixture of 2,3-dimethyl-4-nitropyridine-1-oxide (2.0 g), methyl ethyl ketone (30 ml), 2,2,3,3,3-pentafluoropropanol (3.05 ml), anhydrous potassium carbonate (3.29 g) and hexamethylphosphoric triamide (2.07 g) was stirred while heating at 70° ~ 80° C. for 4.5 days, after which it was subjected to filtration to remove insoluble matters and then concentrated. The residue, after adding water, was extracted with ethyl acetate and dried over magnesium sulfate, after which the solvent was evaporated and the resulting residue was applied on a silica gel (50 g) column, eluted with chloroform-methanol (10:1) and recrystallized from ethyl acetate-hexane to give 2.4 g of 2,3-dimethyl-4-(2,2,3,3-pentafluoropropoxy)pyridine-1-oxide as colorless needles (melting point: 148° ~ 149° C.).

Using the same procedure as described above, the compounds (VIII) were produced using the compounds (VI) as the starting materials.

| Compound (VIII) | | | |
|---|---|---|---|
| $R^2$ | $R^3$ | $R^4$ | Melting point (°C.) |
| $CH_3$ | H | $CH_2CF_3$ | 131.0 ~ 131.5 |
| H | $CH_3$ | $CH_2CF_3$ | 153 ~ 154 |
| H | H | $CH_2CF_2CF_3$ | 79 ~ 81 |
| H | $CH_3$ | $CH_2CF_2CF_3$ | 140 ~ 142 |
| H | H | $CH_2CF_2CF_2H$ | Oily (Note) |
| H | $CH_3$ | $CH_2CF_2CF_2H$ | 143.5 ~ 144.5 |
| $CH_3$ | H | $CH_2CF_2CF_2H$ | 138 ~ 139 |

(Note) NMR(CDCl$_3$)δ: 2.51(3 H,s), 4.39(2 H,tt,J = 1.5, 12 Hz), 6.00(1 H,tt,J = 4, 53 Hz), 6.68–6.88(2 H,m), 8.14(1 H,d,J = 7 Hz)

REFERENCE EXAMPLE 3

To a solution of 2,3-dimethyl-4-(2,2,3,3-tetrafluoropropoxy)pyridine-1-oxide (2.6 g) in acetic anhydride (8 ml), concentrated sulfuric acid (2 drops) was added; and the solution was stirred at 110° C. for 4 hours and then concentrated. The resulting residue was dissolved in methanol (20 ml) and a solution of sodium hydroxide (1.2 g) in water (5 ml) was added, after which the mixture was stirred at room temperature for 30 minutes. After concentration, water was added, and the mixture was extracted with ethyl acetate. The extract was dried over magnesium sulfate and the solvent was evaporated, after which the resulting residue was applied on a silica gel (50 g) column, eluted with chloroform-methanol (10:1) and then recrystallized from isopropyl ether to give 1.6 g of 2-hydroxymethyl-3-methyl-4-(2,2,3,3-tetrafluoropropoxy)pyridine as yellow crystals (melting points: 67°~68° C.).

Using the same procedure as described above, the compounds (X) were produced using the compounds (VIII).

| Compound (X) | | | |
|---|---|---|---|
| $R^2$ | $R^3$ | $R^4$ | Melting point (°C.) |
| H | H | $CH_2CF_3$ | Oily (Note 1) |
| $CH_3$ | H | $CH_2CF_3$ | 93.5~94.0 |
| H | H | $CH_2CF_2CF_3$ | Oily (Note 2) |
| $CH_3$ | H | $CH_2CF_2CF_3$ | Oily (Note 3) |
| H | $CH_3$ | $CH_2CF_2CF_3$ | 87~89 |
| H | H | $CH_2CF_2CF_2H$ | 88~89 |
| H | $CH_3$ | $CH_2CF_2CF_2H$ | 98~99 |
| $CH_3$ | H | $CH_2CF_2CF_2H$ | 67~68 |

(Note 1) NMR(CDCl$_3$)δ: 4.41(2 H,q,J = 7.5 Hz), 4.73(2 H,s), 5.43(1 H,br), 6.75(1 H,dd,J = 2.6 Hz), 6.95(1 H,d,J = 2 Hz), 8.37(1 H,d,J = 6 Hz)
(Note 2) NMR(CDCl$_3$)δ: 4.46(2 H,t,J = 12 Hz), 4.71(2 H,s), 5.93(1 H,br), 6.75(1 H,dd,J = 3.6 Hz), 6.98(1 H,d,J = 3 Hz), 8.36(1 H,d,J = 6 Hz)
(Note 3) NMR(CDCl$_3$)δ: 2.07(3 H,s), 4.28(1 H,brs), 4.49(2 H,t,J = 12 Hz), 4.67(2 H,s), 6.69(1 H,d,J = 5 Hz), 8.34(1 H,d,J = 5 Hz)

REFERENCE EXAMPLE 4

To a solution of 3,5-dimethyl-4-nitropyridine-1-oxide (2.0 g) in 2,2,3,3,3-pentafluoropropanol (10 g), potassium t-butoxide (2 g) was added gradually at 0° C. over a period of 15 minutes, after which the solution was stirred at 60° C. for 18 hours. The resulting reaction product, after adding chloroform, was subjected to Celite filtration, after which the filtrate was applied on a silica gel (80 g) column, was eluted with ethyl acetate-hexane (1:1) and then with 20% methanol-ethyl acetate and then recrystallized from ether-hexane to give 2.6 g of 3,5-dimethyl-4-(2,2,3,3,3-pentafluoropropoxy)pyridine-1-oxide as crystals (melting point: 89°~91° C.).

Using the same procedure as described above the compounds (XII) were produced using the compounds (XI).

| Compound (XII) | | | |
|---|---|---|---|
| $R^2$ | $R^3$ | $R^4$ | Melting point (°C.) |
| $CH_3$ | H | $CH_2CF_3$ | 82~94 |
| $CH_3$ | $CH_3$ | $CH_2CF_3$ | 138~139 |

REFERENCE EXAMPLE 5

A mixture of 3,5-dimethyl-4-(2,2,3,3,3-pentafluoropropoxy)pyridine-1-oxide (2.5 g) and dimethyl sulfate (1 ml) was heated at 120° C. for 30 minutes and methanol (12.5 ml) was added, after which a solution of ammonium persulfate (4.3 g) in water (20 ml)-methanol (10 ml) was added dropwise at 80° C. over a period of 30 minutes and the mixture was stirred for 30 minutes. After concentration, ice was added and the mixture was neutralized with sodium carbonate, and then was extracted with chloroform. After drying the extract over sodium sulfate, the solvent was evaporated to give 2.2 g of 3,5-dimethyl-2-hydroxymethyl-4-(2,2,3,3,3pentafluoropropoxy)pyridine as oil.

NMR(CDCl$_3$)δ:2.12(3H,s), 2.25(3H,s), 4.25(2H,t,J=12 Hz), 4.59(3H,s-like), 8.20(1H,br).

Using the same procedure as described above, the compounds (X) were synthesized from the compounds (XII).

| Compound (X) | | | |
|---|---|---|---|
| $R^2$ | $R^3$ | $R^4$ | Melting point (°C.) |
| H | $CH_3$ | $CH_2CF_3$ | 116~119 |
| $CH_3$ | $CH_3$ | $CH_2CF_3$ | 62~63 |

REFERENCE EXAMPLE 6

To a solution of 2-hydroxymethyl-3-methyl-4-(2,2,3,3,3-pentafluoropropoxy)pyridine (350 mg) in chloroform (10 ml), thionyl chloride (0.2 ml) was added and the solution was refluxed under heating for 30 minutes, after which it was concentrated. The resulting residue was dissolved in methanol (5 ml) and added to a solution of 2-mercaptobenzimidazole (200 mg) and 28% sodium methoxide (1 ml) in methanol (6 ml), after which it was refluxed under heating for 30 minutes. After evaporating the methanol, water was added and the mixture extracted with ethyl acetate. The resulting extract, after washing with aqueous sodium hydroxide, was dried over magnesium sulfate. After evaporating the solvent, the residue was applied on a silica gel (20 g) column and eluted with ethyl acetatehexane (2:1) and then recrystallized from ethyl acetatehexane to give 370 mg of hemihydrate of 2-[[3-methyl-4-(2,2,3,3,3-pentafluoropropoxy)-2-pyridyl]methylthio]benzimidazole as colorless plates (melting point: 145°~146° C.).

Reactions were carried out between the compounds (IV) and (V) in the same manner as described above to produce the compounds (III).

| Compound (III) | | | | |
|---|---|---|---|---|
| $R^1$ | $R^2$ | $R^3$ | $R^4$ | Melting point (°C.) |
| H | H | H | $CH_2CF_3$ | 138~139 |
| H | $CH_3$ | H | $CH_2CF_3$ | 149~150 |
| H | H | $CH_3$ | $CH_2CF_3$ | 168~170 |
| H | $CH_3$ | $CH_3$ | $CH_2CF_3$ | 151.5~152.0 |
| H | H | H | $CH_2CF_2CF_3$ | 125~126 |
| H | H | $CH_3$ | $CH_2CF_2CF_3$ | 151~152 |
| (Note 1) H | H | H | $CH_2CF_2CF_2H$ | Oily |
| H | $CH_3$ | H | $CH_2CF_2CF_2H$ | 134~135 |
| H | H | $CH_3$ | $CH_2CF_2CF_2H$ | 148~149 |
| H | $CH_3$ | $CH_3$ | $CH_2CF_2CF_3$ | 158~160 |
| (Note 2) 5-$CF_3$ | $CH_3$ | H | $CH_2CF_3$ | 92~93 |
| 5-$OCH_3$ | $CH_3$ | H | $CH_2CF_3$ | 159~160 |
| 5-$OCH_3$ | H | $CH_3$ | $CH_2CF_3$ | 152~153 |

(Note 1) NMR(CDCl$_3$)δ:4.35 (2 H,s), 4.39(2 H,tt,J = 1.5, 12 Hz), 5.98(1 H,tt,J = 4, 52.5 Hz), 6.81(1 H,dd,J = 2, 6 Hz), 6.95(1 H,d,J = 2 Hz), 7.1~7.3(2 H,m), 7.4~7.7(2 H,m), 8.50(1 H,d,J = 6 Hz)
(Note 2) ½ H$_2$O

REFERENCE EXAMPLE 7

To a solution of 2-[[3-methyl-4-(2,2,3,3,3-pentafluoropropoxy)-2-pyridyl]methylthio]benzimidazole (2.2 g) in chloroform (20 ml), a solution of m-chloroperbenzoic acid (*1.3 g) in chloroform (15 ml) was added dropwise while ice-cooling over a period of 30 minutes and the resulting reaction mixture was washed with a saturated aqueous sodium hydrogen carbonate. After drying over magnesium sulfate, the solvent was concentrated. The residue was applied on a silica gel (50 g) column, eluted with ethyl acetate and then recrystallized from acetone-isopropyl ether to give 1.78 g of 2-[[3-methyl-4-(2,2,3,3,3-pentafluoropropoxy)-2-pyridyl]methylsulfinyl]benzimidazole as pale yellow prisms. Melting point: 161°~163° C. (decomposition).

Using the same procedure as described above, the compounds (II) were produced using the compounds (III).

| Compound (II) | | | | |
|---|---|---|---|---|
| $R^1$ | $R^2$ | $R^3$ | $R^4$ | Melting point (°C.) |
| H | H | H | $CH_2CF_3$ | 176~177 |
| H | $CH_3$ | H | $CH_2CF_3$ | 178~182(d) |
| H | H | $CH_3$ | $CH_2CF_3$ | 175~177(d) |
| H | $CH_3$ | $CH_3$ | $CH_2CF_3$ | 177~178(d) |
| H | H | H | $CH_2CF_2CF_3$ | 148~150(d) |
| H | H | $CH_3$ | $CH_2CF_2CF_3$ | 145~148(d) |
| H | H | H | $CH_2CF_2CF_2H$ | 132~133 |
| H | $CH_3$ | H | $CH_2CF_2CF_2H$ | 147~148(d) |
| H | H | $CH_3$ | $CH_2CF_2CF_2H$ | 136~139(d) |
| H | $CH_3$ | $CH_3$ | $CH_2CF_2CF_3$ | 157~159 |
| 5-$CF_3$ | $CH_3$ | H | $CH_2CF_3$ | 161~162(d) |
| 5-$OCH_3$ | $CH_3$ | H | $CH_2CF_3$ | 140.5~142(d) |
| 5-$OCH_3$ | H | H | $CH_2CF_3$ | 162~163(d) |

(Note) (d): Decomposition

EXAMPLE 1

A mixture of 2-[[3-methyl-4-(2,2,2-trifluoroethoxy)-2-pyridyl]methylsulfinyl]benzimidazole (1.40 g), methanol (75 ml) and 42% fluoboric acid (1.25 ml) was heated at 37° C. for 5 minutes and then cooled, after which the separated crystals were collected by filtration and washed with methanol to give 4-methyl-3-(2,2,2-trifluoroethoxy)-5H-pyrido[1',2':4,5][1,2,4]-thiadiazino[2,3-a]benzimidazol-13-ium tetrafluoroborate as light yellow plates (1.19 g). Melting point: 167°~170° C. (decomposition).

NMR($CD_3CN$)δ:9.51(1H,d,J=7.5 Hz), 7.74–7.90(1H,m), 7.70(1H,d,J=7.5 Hz), 7.34–7.64(3H,m), 5.05(2H,q,J=7.5 Hz), 4.89(2H,s), 2.48(3H,s).

EXAMPLE 2

A mixture of 2-[[3-methyl-4-(2,2,3,3-tetrafluoropropoxy)-2-pyridyl]methylsulfinyl]benzimidazole (200 mg), methanol (5 ml) and 42% fluoboric acid (0.125 ml) was warmed at 30° C. for 5 minutes and cooled, after which the separated crystals were collected by filtration to give 4-methyl-3-(2,2,3,3-tetrafluoropropoxy)-5H-pyrido[1',2':4,5][1,2,4]thiadiazino[2,3-a]benzimidazol-13-ium tetrafluoroborate as light yellow needles. Melting point: 168°~170° C. (decomposition).

NMR($CD_3CN$)δ:9.50(1H,d,J=7.5 Hz), 7.84–7.91(1H,m), 7.71(1H,d,J=7.5 Hz), 7.33–7.90(3H,m), 6.37(1H,tt,J=52.5,3.5 Hz), 5.00(2H,t,J=12 Hz), 4.90(2H,s), 2.50(3H,s).

EXAMPLE 3

A mixture of 2-[[3-methyl-4-(2,2,3,3,3-pentafluoropropoxy)-2-pyridyl]methylsulfinyl]benzimidazole (209 mg), methanol (5 ml) and 42% fluoboric acid (0.125 ml) was warmed at 37° C. for 5 minutes and cooled, after which the resulting precipitate was collected by filtration to give 4-methyl-3-(2,2,3,3,3-pentafluoro-propoxy)-5H-pyrido[1',2':4,5][1.2.4]thiadiazino[2,3a]-benzimidazol-13-ium tetrafluoroborate as light yellow plates (195 mg). Melting point: 170°~173° C. (decomposition).

NMR($CD_3CN$)δ: 9.51(1H,d,J=7.5 Hz), 7.76–7.91(1H,m), 7.74(1H,d,J=7.5 Hz), 7.37–7.67(3H,m), 5.14(2H,t,J=12 Hz), 4.90(2H,s), 2.49(3H,s).

EXAMPLE 4

A mixture of 2-[[3-methyl-4-(2,2,2-tetrafluoroethoxy)-2-pyridyl]methylsulfinyl]-5-methoxybenzimidazole (100 mg), methanol (2.5 ml) and 42% fluoboric acid (0.063 ml) was warmed at 37° C. for 5 minutes and cooled, after which the separated crystals were collected by filtration and washed with methanol to give a mixture 9-methoxy-4-methyl-3-(2,2,2-trifluoroethoxy)-5H-pyrido[1',2':4,5][1,2,4]thiadiazino[2,3-a]benzimidazol-13-ium tetrafluoroborate and 10-methoxy-4-methyl-3-(2,2,2-trifluoroethoxy)-5H-pyrido[1',2':4,5][1,2,4]thiadiazino[2,3-a]benzimidazol-13-ium tetrafluoroborate (97 mg) as yellow needles. Melting point: 176°~182° C. (decompositon).

NMR($CD_3CN$)δ: 9.44(1H,d,J=7.5 Hz), 6.97–7.73(4H,m), 5.01(2H,q,J=9 Hz), 4.85(2H,s), 3.87 and 3.89 (3H, s and s), 2.47(3H,s).

EXAMPLE 5

A mixture of 2-[[3-methyl-4-(2,2,2-trifluoroethoxy)-2-pyridyl]methylsulfinyl]benzimidazol (140 mg), methanol (4.9 ml) and concentrated hydrochloric acid (0.1 ml) was warmed at 37° C. for minutes, after which the resulting precipitate was collected by filtration to give 4-methyl-3-(2,2,2-trifluoroethoxy)-5H-pyrido[1',2':4,5][1,2,4]thiadiazino[2,3-a]benzimidazol-13-ium chloride (74 mg). Melting point: 160°~170° C. (decomposition).

What we claim is:

1. A compound of the formula

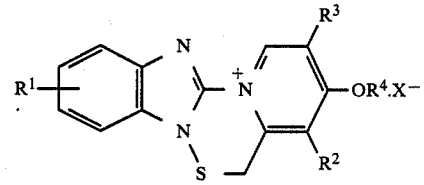

wherein $R^1$ is hydrogen, methoxy or trifluoromethyl, $R^2$ and $R^3$ are the same or different and are each hydrogen or methyl, $R^4$ is a fluorinated lower alkyl having 2 to 5 carbon atoms and 1 to 11 fluorine atoms and $X^-$ is a pharmaceutically acceptable anion, respectively.

2. A compound as claimed in claim 1, wherein $R^1$ is hydrogen.

3. A compound as claimed in claim 1, wherein $R^1$ is methoxy.

4. A compound as claimed in claim 1, wherein $R^2$ is methyl.

5. A compound as claimed in claim 1, wherein $R^3$ is hydrogen.

6. A compound as claimed in claim 1, wherein $R^4$ is 2,2,2-trifluoroethyl.

7. A compound as claimed in claim 1, wherein $R^4$ is 2,2,3,3-tetrafluoropropyl.

8. A compound as claimed in claim 1, wherein $X^-$ is tetrafluoroborate ion.

9. A compound as claimed in claim 1, wherein $X^-$ is chloride ion.

10. A compound as claimed in claim 1, wherein the compound is 4-methyl-3-(2,2,2-trifluoroethoxy)-5H-pyrido-[1',2':4,5][1,2,4]thiadiazino[2,3-a]benzimidazol-13-ium tetrafluoroborate.

11. A compound as claimed in claim 1, wherein the compound is 4-methyl-3-(2,2,3,3-tetrafluoropropoxy)-

5H-pyrido[1',2':4,5][1,2,4]thiadiazino[2,3-a]benzimidazol-13-ium tetrafluoroborate.

12. A compound as claimed in claim 1, wherein the compound is 4-methyl-3-(2,2,3,3,3-pentafluoropropoxy)-5H-pyrido[1',2':4,5][1,2,4]thiadiazino[2,3-a]benzimidazol-13-ium tetrafluoroborate.

13. A compound as claimed in claim 1, wherein the compound is 9-methoxy-4-methyl-3-(2,2,2-trifluoroethoxy)-5H-pyrido[1',2':4,5][1,2,4]thiadiazino[2,3-a]benzimidazol-13-ium tetrafluoroborate.

14. A compound as claimed in claim 1, wherein the compound is 10-methoxy-4-methyl-3-(2,2,2-trifluoroethoxy)-5H-pyrido[1',2':4,5][1,2,4]thiadiazino[2,3-a]benzimidazol-13-ium tetrafluoroborate.

15. A compound as claimed in claim 1, wherein the compound is 4-methyl-3-(2,2,2-trifluoroethoxy)-5H-pyrido[1,2:4,5][1,2,4]thiadiazino[2,3-a]benzimidazol-13-ium chloride.

* * * * *